United States Patent [19]

Deletis

[11] Patent Number: 5,081,990
[45] Date of Patent: Jan. 21, 1992

[54] CATHETER FOR SPINAL EPIDURAL INJECTION OF DRUGS AND MEASUREMENT OF EVOKED POTENTIALS

[75] Inventor: Vedran Deletis, Edison, N.J.

[73] Assignee: New York University, New York, N.Y.

[21] Appl. No.: 522,008

[22] Filed: May 11, 1990

[51] Int. Cl.⁵ .................................................. A61N 1/05
[52] U.S. Cl. .................................. 128/642; 128/741; 128/784
[58] Field of Search ............... 128/642, 784, 785, 786, 128/740, 741, 905, 739

[56] References Cited

U.S. PATENT DOCUMENTS

| | | | |
|---|---|---|---|
| 3,817,341 | 6/1974 | Grausz | 180/14.6 |
| 4,014,317 | 3/1977 | Bruno | 600/18 |
| 4,073,287 | 2/1978 | Bradley et al. | 128/642 |
| 4,360,031 | 11/1982 | White | 128/786 |
| 4,633,889 | 1/1987 | Talalla et al. | 128/784 |
| 4,711,251 | 12/1987 | Stokes | 128/784 |
| 4,818,662 | 4/1989 | Heil, Jr. et al. | 128/786 |
| 4,832,048 | 5/1989 | Cohen | 128/786 |

FOREIGN PATENT DOCUMENTS 3602219 7/1987 Fed. Rep. of Germany ...... 128/784

Primary Examiner—William E. Kamm
Assistant Examiner—Scott M. Getzow
Attorney, Agent, or Firm—Browdy and Neimark

[57] ABSTRACT

An spinal epidural catheter apparatus and method are shown and described. The apparatus provides for injection of drugs into the spinal epidural area, and measurement of evoked potentials at the point of injection by means of electrodes located on the tip of the catheter and a voltage detector connected to the free end of the catheter.

15 Claims, 3 Drawing Sheets

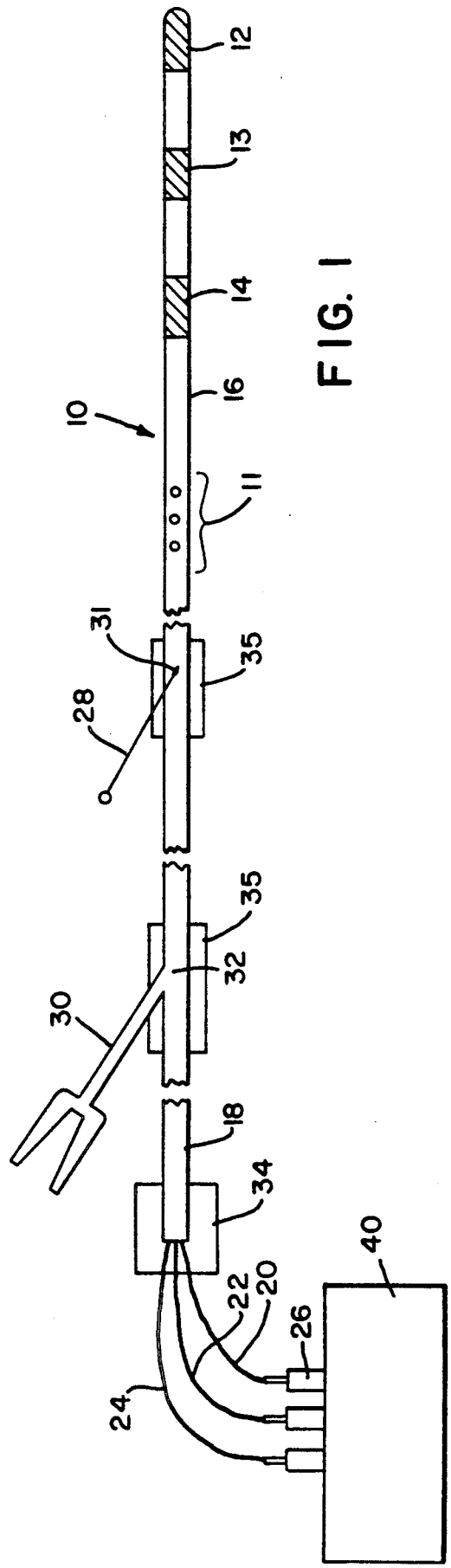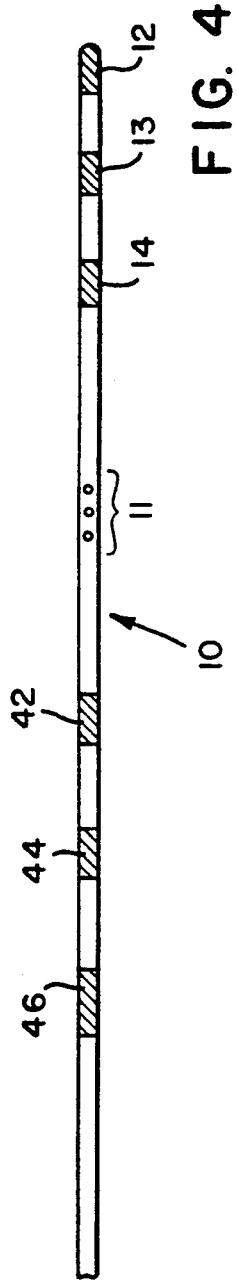

CATHETER FOR SPINAL EPIDURAL INJECTION OF DRUGS AND MEASUREMENT OF EVOKED POTENTIALS

FIELD OF THE INVENTION

This invention is for use in applying drugs in the spinal epidural area of a patient, and for measuring the electrical response of the patient's spinal cord to the injected drugs.

BACKGROUND OF THE INVENTION

It is well known to provide catheters which permit the injection of fluids in the body as well as measurement of electrical activity of different organs or muscles. While these prior art catheters have been used in various areas of the body, they have not been used in applying medication to and detecting evoked responses from the spinal epidural area.

Grausz U.S. Pat. No. 3,817,241 shows a catheter which both supplies a fluid, such as from an I.V. bottle 27, and provides a probe which may extend into the patient's artery or vein. Probe 16 and 17 senses EKG activity and/or provides shocking for pacing of the heart.

Bradley U.S. Pat. No. 4,073,287 et al. teaches the use of a catheter for performing urethral profilometry. The catheter is provided with a fluid entrance 22 for inserting fluid into the body, and a connector plug 16 which is connected to electrodes 18 and 19. The electrodes 18 and 19 band around the tube, and provide electrical contact to the urethral tissue.

White U.S. Pat. No. 4,360,031 shows the use of a drug dispensing and irrigatable electrode. This device is for use in heart treatment.

U.S. Pat. Nos. 4,819,661 to Heil, Jr. et al., 4,013,317 to Bruno, 4,832,048 to Cohen and 4,711,251 to Stokes show other examples of catheters, suction devices, and probes which include electrical leads for testing of body reactions or functions.

The use of electrodes for electrophysiological monitoring of the spinal cord during spinal surgery, and particularly for measurement of motor and somatosensory function, is known (Jones et al, "A system for the electrophysiological monitoring of the spinal cord during operations for scoliosis," *J. Bone Joint Surg.*, 65-B, 134-139 (1983); Boyd et al, "A method of monitoring function in corticospinal pathways during scoliosis surgery with a note on motor conduction velocities," *J. Neurol. Neurosurg. Psychiat.*, 49, 251-257 (1986)). For this purpose electrodes are placed in the spinal cord area during surgery. Machida et al, "Spinal cord monitoring—Electrophysiological measures of sensory and motor function during spinal surgery," Spine, 10 (1985), disclose the use of two sets of electrodes on the spinal cord during surgery, one for transmitting stimuli and the other for recording evoked potential. However, two separate electrode arrays were necessary for this purpose.

SUMMARY OF THE INVENTION

In the present invention, a catheter having electrodes on the tip is used to provide simultaneously drugs as well as a means to measure the effect of the drugs on spinal cord electrical activity. As a spinal epidural catheter, this device must be much smaller in diameter than prior art devices, such as those discussed above, which are used for heart treatment or other intravenous or urethral applications.

In the present device, the electrical contacts are integrally mounted on a drug applicating tube so that the electrodes do not move with respect to the tube. A small inexpensive disposable tube is preferably used which may readily be injected into the spinal epidural cavity.

While the catheter will normally be sufficiently rigid to permit epidural placement, if the materials used do not permit sufficient rigidity for this purpose, a stylet may be used to control the placement of the catheter. In this case a stylet passage is present which permits insertion of the stylet into the catheter.

The catheter size is preferably that of a number 4 French body (1.67 mm). The useable length of the catheter is not critical and may be approximately 45-180 cm. Preferably, the length of the catheter is such that it may conveniently reach to the amplifier of the recording device during use. One or more electrodes are disposed at the tip end of the catheter, preferably separated by approximately 1-2 centimeters. For use as a spinal epidural catheter, the catheter electrode should pass through a 15 gauge epidural needle. Preferably, the catheter should be of an even smaller diameter so that it may pass through a 17 or 18 gauge needle.

The catheter is provided with a separate lumen through which drugs may pass, which lumen is separate from the region through which the electrode leads pass. The drug insertion lumen terminates at the proximal end of the catheter preferably with a Luer connector which may connect to a standard hypodermic syringe. The drug insertion lumen terminates at one or more small holes in the wall of the catheter, preferably two holes, proximal to the electrode farthest from the tip of the catheter. It is preferred that the drug be applied into the epidural space of the spinal cord between the point of electrical stimulus and the electrodes. Thus, the application holes may be about 2 cm to about 20 cm from the electrode farthest from the tip, preferably about 4-8 cm therefrom. Alternatively, the catheter may be supplied with two sets of electrodes, one set on either side of the drug application openings. Depending on the locus of the stimulus, the set of electrodes is activated which is on the opposite side of the locus of drug insertion in the direction of travel of the electrical stimulus along the spine. Each lead is separately labeled to identify the particular electrode to which it is connected. All of the electrode leads are preferably fed to a controller which determines which of the electrodes are to be monitored at any given time.

BRIEF DESCRIPTION OF THE DRAWING

FIG. 1 shows an epidural catheter in accordance with the present invention.

FIG. 4 shows an alternative embodiment of the catheter of the present invention.

DETAILED DESCRIPTION OF PREFERRED EMBODIMENTS

Figure 2:
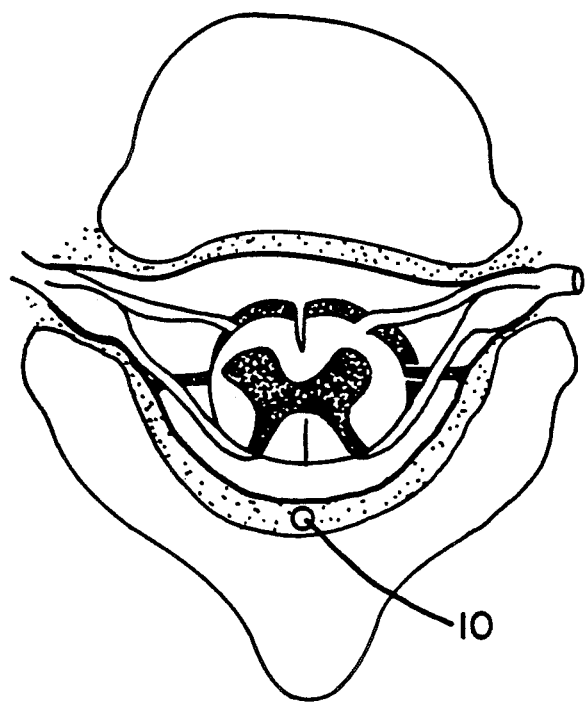
FIG. 2 shows a cross section of the spine with the catheter 10 in place.

The epidural catheter of the present invention provides for measurement of motor and somatosensory evoked potentials as well as reflex activity of the spinal cord in the electrode-containing region of the catheter, simultaneously with the application of drugs. By means of this catheter, epidural evoked potentials may be monitored prior to, during and after administration of drugs to the spinal area.

In FIG. 1, the catheter 10 is shown with contacts 12, 13 and 14 at the tip. These contacts are preferably made of platinum, but could be platinum-iridium combination, stainless steel, or any other low impedance, biologically acceptable conductor. The contacts extend around the catheter and are separated by approximately 1-2 centimeters. The number of electrodes on the catheter tip is not critical. There are preferably at least two so that one will serve as the recording electrode and one as the reference electrode. Use of more than two electrodes permits readings even if one or more becomes occluded or is poorly placed or otherwise becomes inoperative. It is also possible to have only a single electrode with the device having another external electrode for use as the reference electrode which, for example, may be placed under or on the skin during use.

The diameter of the catheter tube 16 is necessarily small in size, such as a French size number 4, or of a diameter small enough to fit through either a gauge 15 or gauge 16, 17 or 18 epidural needle. The rear section of the catheter 18 which is not inserted into the epidural space may be any convenient size. Attached to the leads 20, 22 and 24 are connecting sockets 26 which permit attachment of the catheter to any convenient electronic measuring and controlling equipment 40 which may be used for receiving the signals picked up by electrodes 12, 13 and 14 and measuring evoked potentials across the electrodes 12, 13 and 14. Male pin connectors 26 may be appropriately marked so that the identity of contacts 12, 13 and 14 may be determined. The equipment 40 may include controlling and computing functions to select the appropriate electrodes to be activated, and calculate and display results. The equipment 40 may also be capable of transmitting electrical signals to the electrodes so as to provide the evoked potential stimuli. Thus, the stimuli can be applied at the spinal cord and read externally at the head or extremities.

A stylet 28 may be inserted into the catheter via passage 31 for purposes of manipulating the catheter during placement in the epidural region. Generally, however, no use of a stylet 28 is necessary as the material used to make the electrodes is sufficiently rigid to allow placement without use of a stylet.

Drugs (medicaments) are inserted into the epidural region by the catheter by injection from a drug administering device, such as a hypodermic syringe, to passage 30 which directs the drug to the interior of the catheter. The drug exits the catheter through outlet openings 11. The drug passage may be made of Teflon and comprise a Teflon sheath. Surrounding the intersection of the stylet passage 31 (if present) and the catheter, and surrounding the drug passage 32 and the catheter, are heat shrunk plastic compositions 35 which seal and maintain the relative positions of the tubes and the alignment of the passages.

The wires 22, 20 and 24 between the electrodes 12, 13 and 14 and the rear of the device may be any suitable wire with sufficient flexibility and size, preferably multi-core wires.

Also located at the rear of the catheter is a heat shrunk plastic protector 34 which is used to provide the transition from the catheter tubing 18 to the wires 20, 22 and 24, and connectors 26.

Figure 3:
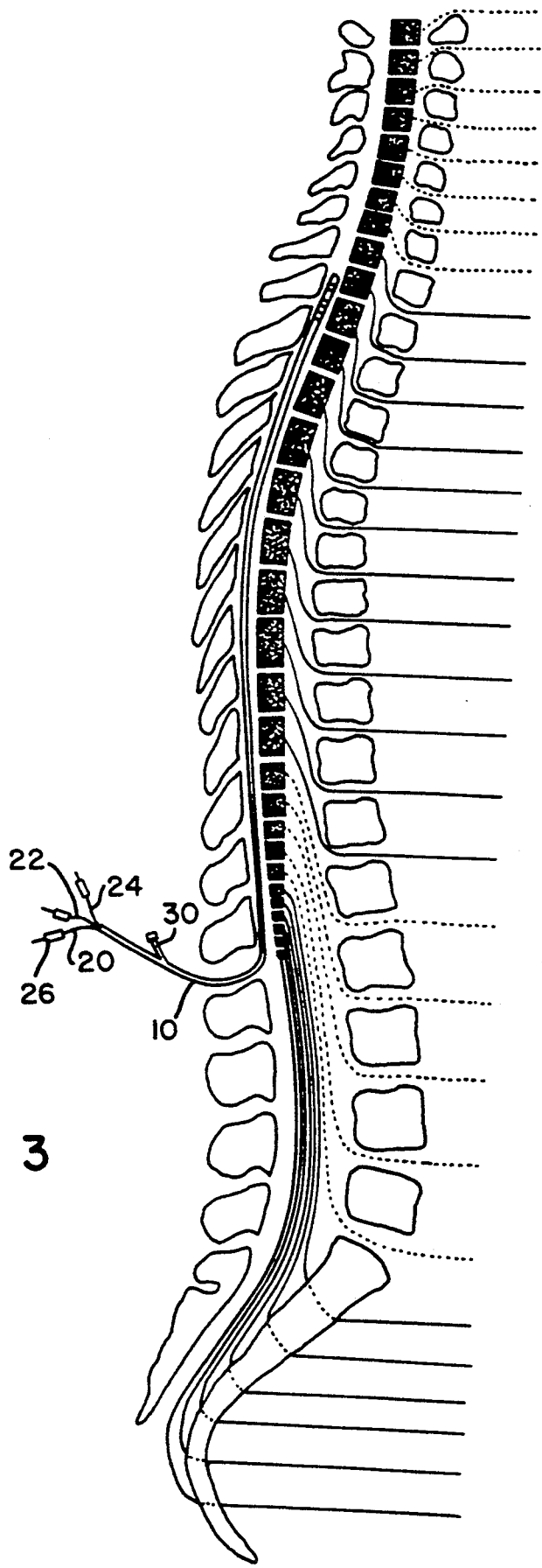
FIG. 3 shows insertion of catheter 10 into the spine as viewed along the length of the spine.

The usable length of the catheter is approximately 45-180 centimeters long and the catheter may include marks along its length (not shown) to identify the distance to the tip. The catheter, when in use, is inserted into the spinal epidural space as seen in FIGS. 2 and 3. This may be accomplished by means of a 15 gauge epidural needle or it may be applied directly during spinal surgery.

The epidural catheter of the present invention is preferably used to record spinal evoked potentials before and after application of different medicaments in order to give an objective technique for measurement of the amount of drugs applied in the patient's epidural space rather than the subjective method of clinical examination. By electrical stimulation of the peripheral nerves of the lower or upper extremities (depending where the epidural catheter was placed) it is possible to measure the electrical activity of the spinal cord—"spinal evoked potentials". This activity indicates the conductivity of the ascending (somatosensory) pathways of the spinal cord transmitting information from the body to the brain. In the same way, the electrical activity of the descending (motor) pathways in the spinal cord arriving from the brain can be recorded in the epidural space of the spinal cord when elicited by electrical or magnetic stimulation of the motor cortex of the brain. By this approach, the influence of drugs on the descending motor activity of the spinal cord can be examined, after application of the drug in the epidural space.

In the embodiment shown in FIG. 4, the catheter 10 is the same as that shown in FIG. 1, and thus bears the same reference numerals, except for the presence of an additional set of electrodes 42, 44, 46 proximal to the drug outlet openings 11. Since it is difficult to apply a catheter in a descending direction in the spinal epidural cavity without surgery, the presence of two sets of electrodes allows monitoring the effects of drugs applied in the patient's epidural space on either the ascending or the descending spinal cord pathways. Furthermore, the same catheter can be used to measure both. Electrodes 42, 44 and 46 are connected via leads 48, 50, 52 to the electronic measuring and controlling equipment 40.

Because the two arrays of electrodes, 12, 13 and 14 on the one hand and 42, 44 and 46 on the other, can each be used as recording electrodes or stimulus electrodes, the catheter 10 can be used not only to record evoked potential of electrical or mechanical stimuli applied to the head or extremities, but they can be used to directly stimulate the spinal cord with the cortical somatosensory evoked potentials measured over the scalp or the motor responses recorded over appropriate muscles. Indeed, one array of electrodes, such as 42, 44 and 46, can be used to stimulate the spinal cord directly by applying electrical stimuli and the other array of electrodes, 12, 13 and 14, can be used to detect activity over different pathways of the spinal cord. Thus, the present catheter can be used to replace the separate arrays of electrodes used by Machida (1985), supra, for example.

The equipment 40 to which the catheter is attached can readily be constructed by those of ordinary skill in the art as it is similar to related equipment for prior art external electrodes used to measure evoked potentials. Indeed, off-the-shelf equipment, such as the "Nicolet Pathfinder" of Nicolet Biomed Instr., Madison, Wis., the "Cadwell Quantum 84" of Cadwell Lab, Kennwick, Wash., the "Counterpoin" of Dantec Electronics, Annandale, N.J. and the "Sentinel-4" of Axon System Corp., Deer Park, N.Y., may be used for this purpose. Equipment 40 must be capable of receiving and transmitting electrical signals to and from any preselected pairs of electrodes. Furthermore, it includes the capability of recording and processing the data obtained and outputting results, for example, in the form of a display. While one schematic box is shown for equipment 40, it should be understood that such was merely used for convenience as the crux of the present invention lies in the structure of the catheter itself, not in the controlling equipment. Accordingly, those of ordinary skill in the art will readily understand that many pieces of equipment may be used and associated with one another to make up the equipment 40, including recording equipment, stimulation equipment, display equipment, isolation equipment, processing equipment, etc.

One of the major specific applications for the catheter in accordance with the present invention is in the monitoring of epidural anesthesia during childbirth or spinal surgery. The epidural catheter is placed percutaneously into the epidural space using a 15 gauge epidural needle and medicaments such as morphine or local anesthetic are applied into the epidural space through the drug application tube 30 and outlets 11. The medicament will then produce the desired effect on the spinal cord. Electrical stimulation is then applied to the peripheral nerves of the upper extremities and the spinal evoked potentials are measured at the electrodes which are downstream of the drug administration site in the direction of stimulus travel in the spinal cord. Spinal evoked potentials recorded with the epidural catheter of the present invention before and after application of the medicament give an objective technique for measurement of the amount of drug applied in the patient's epidural space rather than the subjective method of clinical examination. Such an objective technique is critical in the determination of the amount of morphine added in the epidural space during delivery, for example, or the amount of local anesthetic required for pain relief during different kinds of surgery where epidural spinal anesthesia is used. By means of such objective measurement, the proper amount of anesthesia can be assured to maintain the desired anaesthetic effect without overloading the patient. Particularly during delivery it is not desirable for the health of the newborn infant to use too much epidurally applied drugs.

Another utility for the catheters of the present invention is in measurement of the reflex activity of the spinal cord (monosynaptic reflex) before and after application of drugs for the relief of spasticity. Thus, one can determine the optimal amount of drug required for the best results.

When the catheter is used during surgical procedures on the spinal cord, where the bone cover is removed, the epidural catheter can be placed in the epidural space directly. By recording the electrical activity of the spinal cord one can monitor the integrity of the spinal cord, already recognized as a method for the intraoperative monitoring of spinal evoked potentials. A similar method has previously been used for the prevention of neurological deficits during spinal cord surgery (see Jones et al (1983), supra, and Boyd et al (1986), supra.

The catheter of the present invention may be used not only on human patients but also on other animals, preferably vertebrates, and most preferably mammals. As animals other than humans cannot communicate, an objective means of monitoring the effect of local anesthesia becomes very valuable.

The particular material of which the catheter is made is not critical and may be any of the types of material used in known catheters, such as known bipolar cardiac pacing catheters. The electrical leads may be passed through the catheter in any known manner, such as within the wall of the tubular member of the catheter.

The sizing and dimensioning of the catheter of the present invention is critical in order to permit its insertion into the epidural space to perform the functions described herein. Known cardiac or urethral catheters which may have electrodes and drug administration openings do not fall within the definition of the present invention if they are not sized and dimensioned in order to permit their insertion into the epidural space of the spinal cord as described and claimed herein.

It should be understood that the terms "distal" and "proximal" as used herein mean the following. The distal end of the catheter is the tip of the catheter which is first inserted into the spinal cord, i.e., the location of electrode 14 in FIG. 1. The proximal end is the opposite end of the catheter. The distal direction is the direction leading toward the distal end and the proximal direction is the direction leading toward the proximal end.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for determining the effect of epidurally administered drugs on the spinal cord electrical activity of an animal, comprising the steps of:
    (1) insertion of a catheter into the epidural space of the spinal cord, said catheter having at least two electrodes and a means for injecting drugs;
    (2) administration of a drug through said catheter into the epidural space;
    (3) administering an electrical stimulus to the animal;
    (4) detecting the evoked response at the electrodes of said catheter; and
    (5) comparing said detected response with the response detected in the same animal when drugs have not been inserted into the epidural space.

2. A method in accordance with claim 1, wherein the animal is a human.

3. A device for epidurally administering a drug to the spine of an animal and measuring spinal cord electrical activity, comprising:
    a catheter sized and dimensioned for insertion into the spinal epidural space and having a distal tip and a proximal end, said catheter having drug passage means for passage of a drug through the catheter and including an outlet opening for allowing the drug to exit the catheter into the epidural space when the catheter is in use, and said catheter further having first electrode means and second electrode means, both being connectable by means of separate electrical connections within the catheter to an external electrical transmission or reception device, wherein said first electrode means is disposed at or near the distal tip of the catheter and distal to said outlet opening, and said second electrode means is disposed proximal to said outlet opening.

4. A device in accordance with claim 3, wherein the portion of said catheter intended to be inserted into the spinal epidural space when in use is small enough to pass through a 15-gauge epidural needle.

5. A device in accordance with claim 3, wherein the portion of said catheter intended to be inserted into the spinal epidural space when in use is small enough to pass through an 18-gauge epidural needle.

6. A device in accordance with claim 3, wherein said first electrode means includes at least two electrodes, each being separately electrically connectable to the external electrical transmission or reception device.

7. A device in accordance with claim 6, wherein one electrode of said first electrode means is disposed at the distal tip of the catheter and each additional electrode of said first electrode means is disposed approximately one centimeter from the electrode next distal thereto.

8. A device in accordance with claim 7, wherein said drug passage means outlet opening is disposed about 2 to about 20 cm proximal to the electrode farthest from the distal tip of the catheter.

9. A device in accordance with claim 3, wherein said catheter is sized and dimensioned for insertion into the spinal epidural space of a human patient.

10. A method for monitoring the effect of spinal epidural anaesthesia using a device for epidurally administering a drug to the spine of an animal and measuring spinal cord electrical activity, comprising:

a catheter sized and dimensioned for insertion into the spinal epidural space and having a distal tip and a proximal end, said catheter having drug passage means for passage of a drug through the catheter and including an outlet opening for allowing the drug to exit the catheter into the epidural space when the catheter is in use, and said catheter further having first electrode means and second electrode means, both being connectable by means of separate electrical connections within the catheter to an external electrical transmission or reception device, wherein said first electrode means is disposed at or near the distal tip of the catheter and distal to said outlet opening, and said second electrode means is disposed proximal to said outlet opening, said method comprising:

inserting the catheter into the spinal epidural space of the animal to be anesthetized until the drug passage means outlet opening is at the desired location;

administering anaesthetic via said drug passage means, through said outlet opening, into the epidural space;

applying triggered electrical stimuli by means of one of said first and second electrode means;

measuring the evoked potential at the other of said first and second electrode means; and adjusting the amount of anaesthetic being administered dependent on the nature of the measured evoked potential to assure that sufficient anaesthetic is being administered for the desired anaesthetic effect without overloading the animal with anaesthesia.

11. A method in accordance with claim 10, wherein the animal is a human.

12. A device in accordance with claim 13, wherein said second electrode means includes at least two electrodes, each being separately electrically connectable to the external electrical transmission or reception device.

13. A device in accordance with claim 2, wherein the animal is a human.

14. A method for monitoring the effect on an animal of spinal epidural anaesthesia using a device comprising a catheter sized and dimensioned for insertion into the spinal epidural space of the animal to be anesthetized, said catheter having drug passage means for passage of a drug through the catheter and including an outlet opening for allowing the drug to exit the catheter into the epidural space when the catheter is in use, and said catheter further having first electrode means disposed at or near the distal tip of the catheter, said first electrode means being connectable by means of an electrical connection within the catheter to an external electrical transmission or reception device, the method comprising:

inserting the catheter into the spinal epidural space of the animal to be anesthetized until the drug passage means outlet opening is at the desired location;

administering anaesthetic via said drug passage means, through said outlet opening, into the epidural space;

applying triggered electrical or mechanical stimuli to the animal;

measuring the evoked potential at said electrode means; and adjusting the amount of anaesthetic being administered dependent on the nature of the measured evoked potential to assure that sufficient anaesthetic is being administered for the desired anaesthetic effect without overloading the animal with anaesthesia.

15. A method in accordance with claim 14, wherein the animal is a human.

* * * * *